(12) United States Patent
Medero et al.

(10) Patent No.: US 7,070,566 B2
(45) Date of Patent: Jul. 4, 2006

(54) ARTIFACT REJECTION USING PULSE QUALITY VALUES

(75) Inventors: Richard Medero, Tampa, FL (US); Lawrence T. Hersh, Tampa, FL (US); Sai Kolluri, Tampa, FL (US); Bruce A. Friedman, Tampa, FL (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 676 days.

(21) Appl. No.: 10/387,631

(22) Filed: Mar. 13, 2003

(65) Prior Publication Data

US 2004/0181157 A1    Sep. 16, 2004

(51) Int. Cl.
*A61B 5/00* (2006.01)

(52) U.S. Cl. .................. 600/494; 600/490; 600/496

(58) Field of Classification Search .............. None
See application file for complete search history.

(56) References Cited

U.S. PATENT DOCUMENTS

| | | | |
|---|---|---|---|
| 4,360,029 A | 11/1982 | Ramsey, III | 128/681 |
| 4,543,962 A | 10/1985 | Medero et al. | 128/682 |
| 4,638,810 A | 1/1987 | Ramsey, III et al. | 128/681 |
| 4,796,184 A | 1/1989 | Bahr et al. | 364/413.03 |
| 4,889,133 A | 12/1989 | Nelson et al. | 128/681 |
| 4,949,710 A | 8/1990 | Dorsett et al. | 128/680 |
| 5,579,776 A | 12/1996 | Medero | 128/680 |
| 5,704,362 A | 1/1998 | Hersh et al. | 128/680 |
| 5,931,790 A * | 8/1999 | Peel, III | 600/494 |
| 6,358,213 B1 | 3/2002 | Friedman et al. | 600/493 |
| 6,423,010 B1 | 7/2002 | Friedman et al. | 600/494 |
| 6,440,080 B1 | 8/2002 | Booth et al. | 600/494 |
| 2002/0082507 A1 | 6/2002 | Kolluri et al. | |
| 2004/0059234 A1* | 3/2004 | Martin et al. | 600/500 |

FOREIGN PATENT DOCUMENTS

| | | |
|---|---|---|
| EP | 0536782 | 10/1992 |
| EP | 1077042 A1 | 2/2001 |
| EP | 1 195 133 | 4/2002 |

* cited by examiner

*Primary Examiner*—Robert L. Nasser
(74) *Attorney, Agent, or Firm*—Andrus, Sceales, Starke & Sawall LLP

(57) ABSTRACT

A method and system for making pulse rate and blood pressure determinations is disclosed. The method and system comprise collecting oscillometric blood pressure data from pulses, determining individual quality values for feature measurements of the pulses, obtaining an overall quality assessment based on the individual quality values, repeating the collecting step until overall quality level is satisfied, and determining blood pressure and pulse rate using the individual quality values.

36 Claims, 14 Drawing Sheets

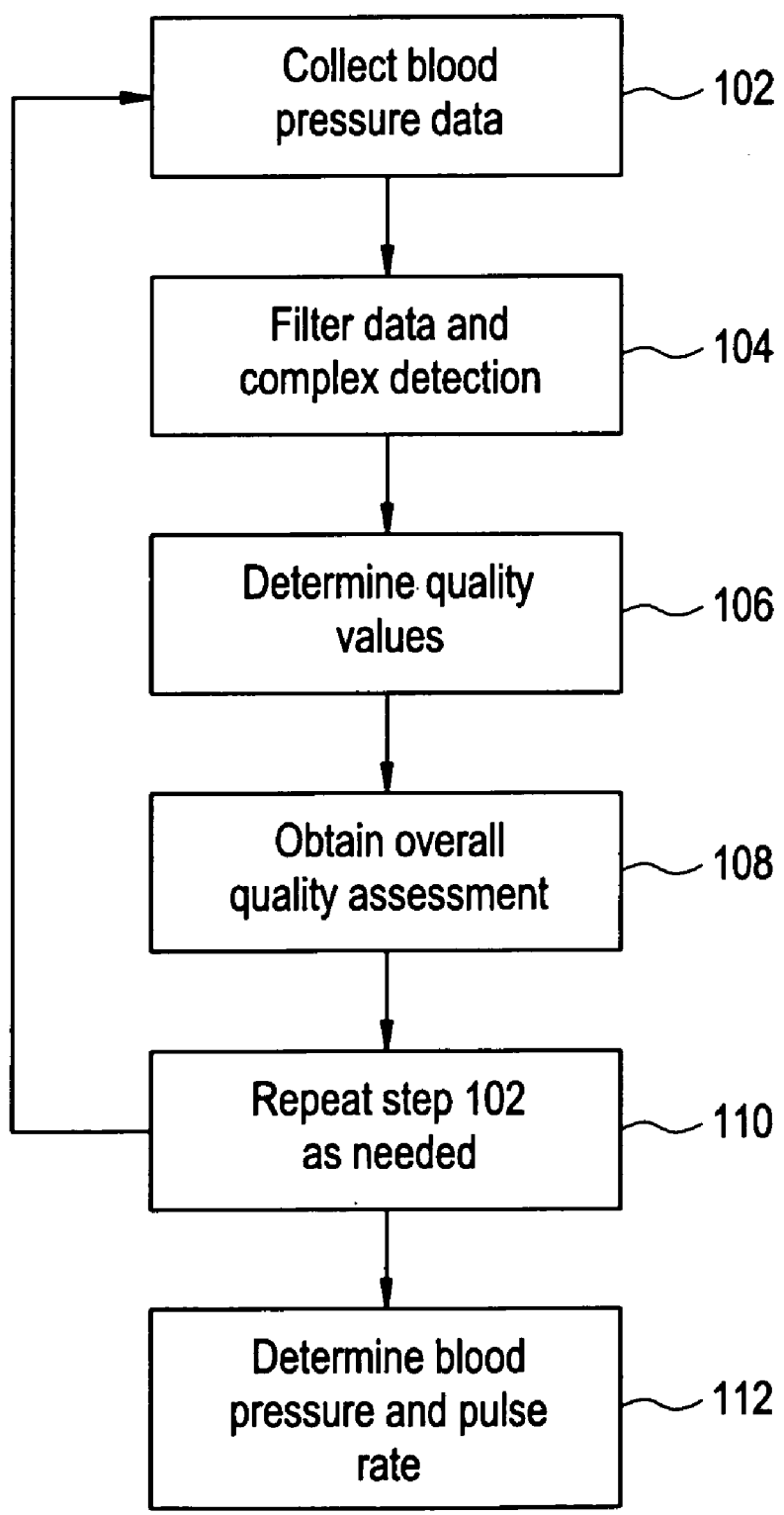

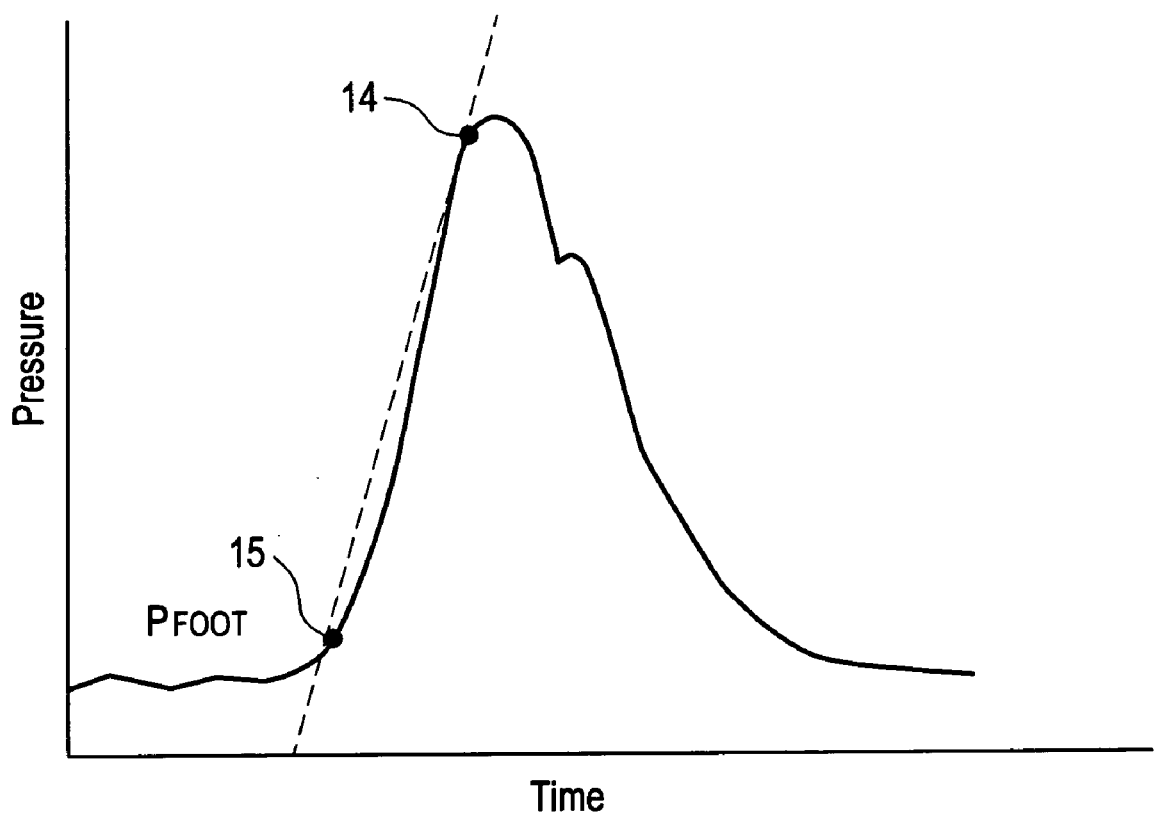

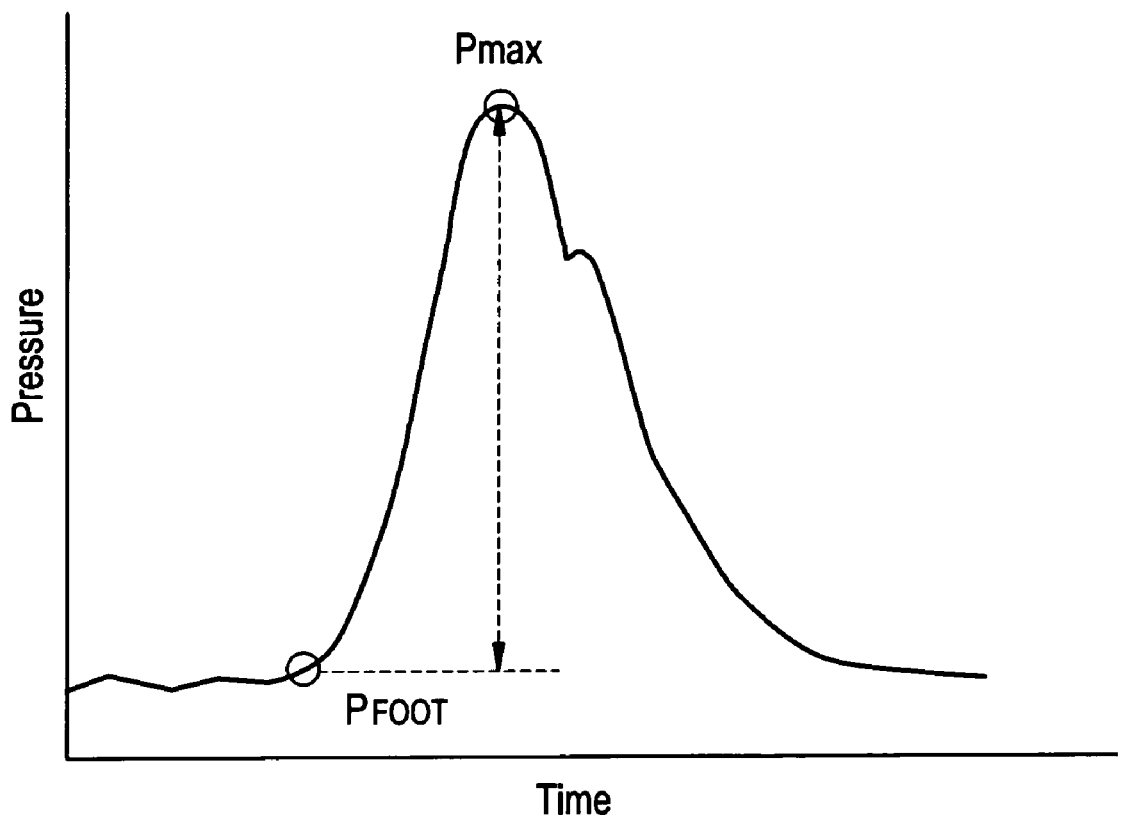

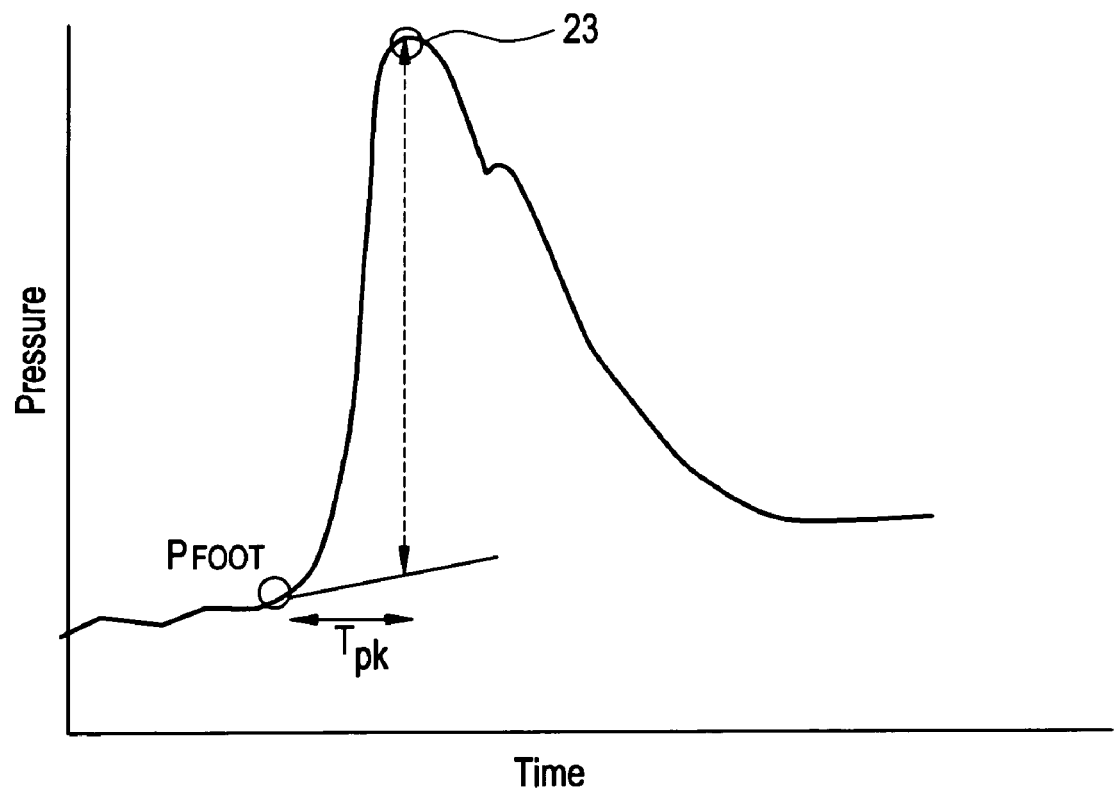

Complex-Time to Peak

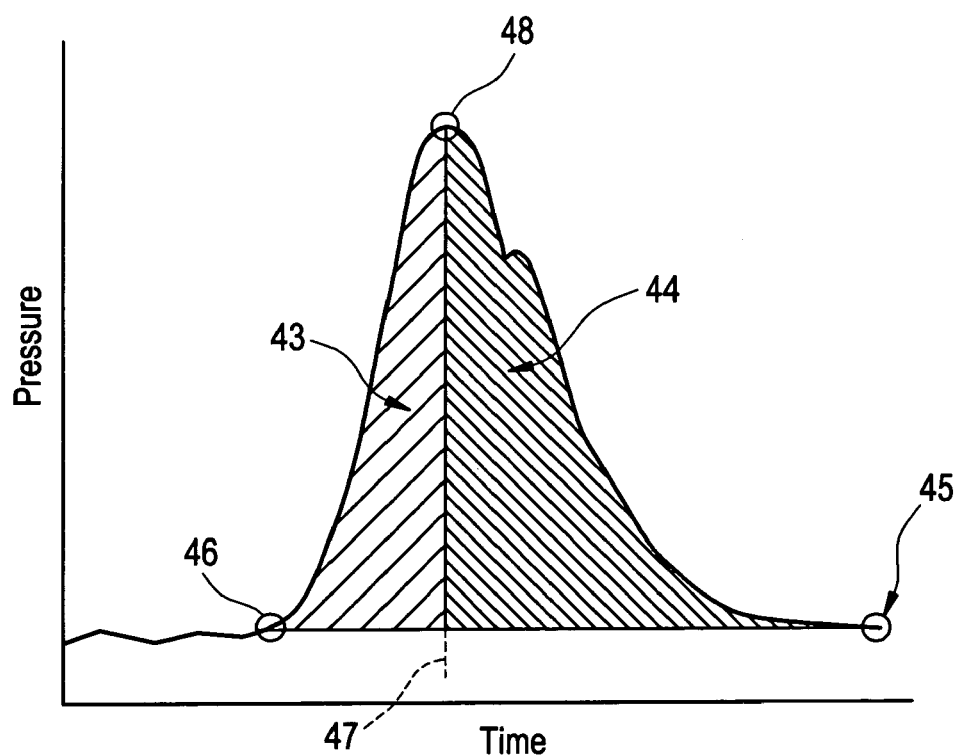

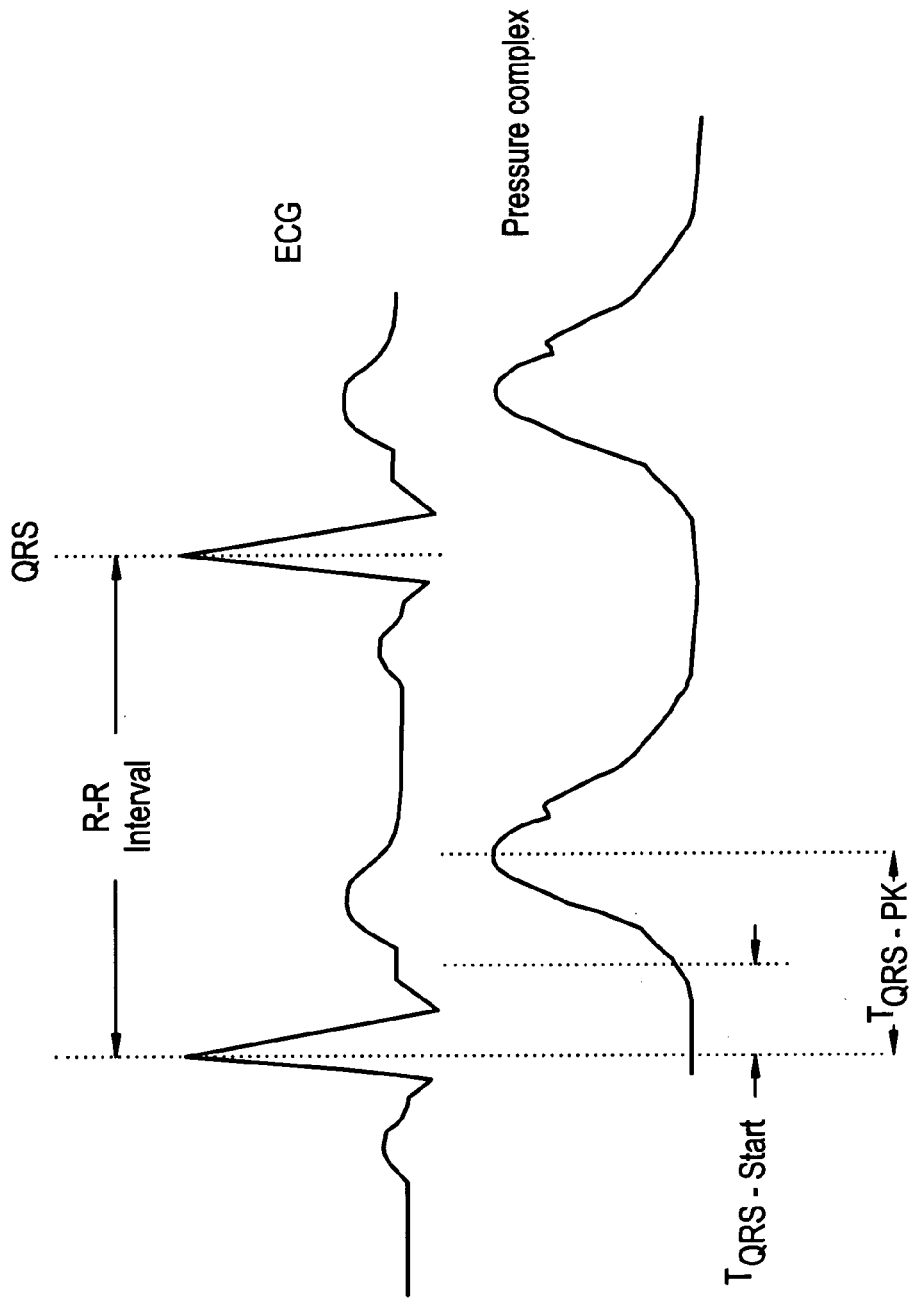

Dual channel filtering

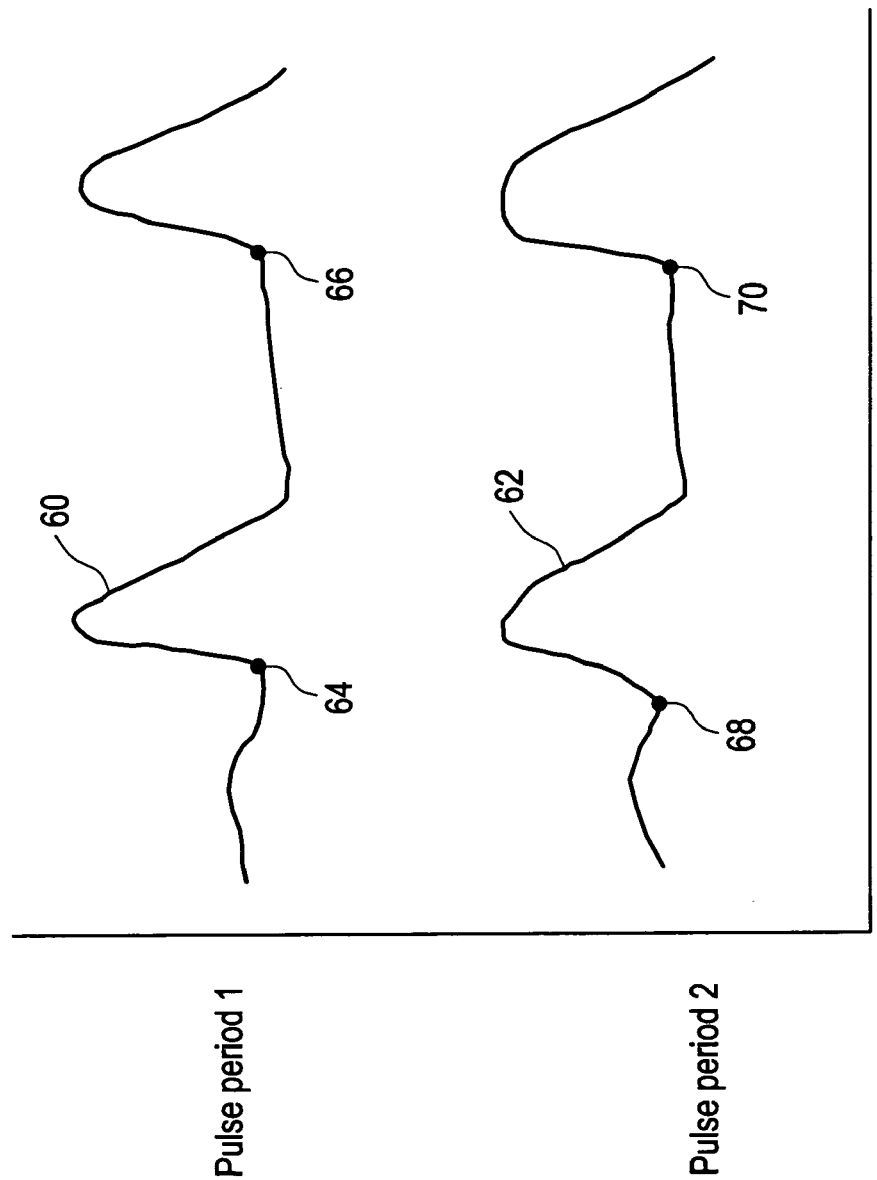

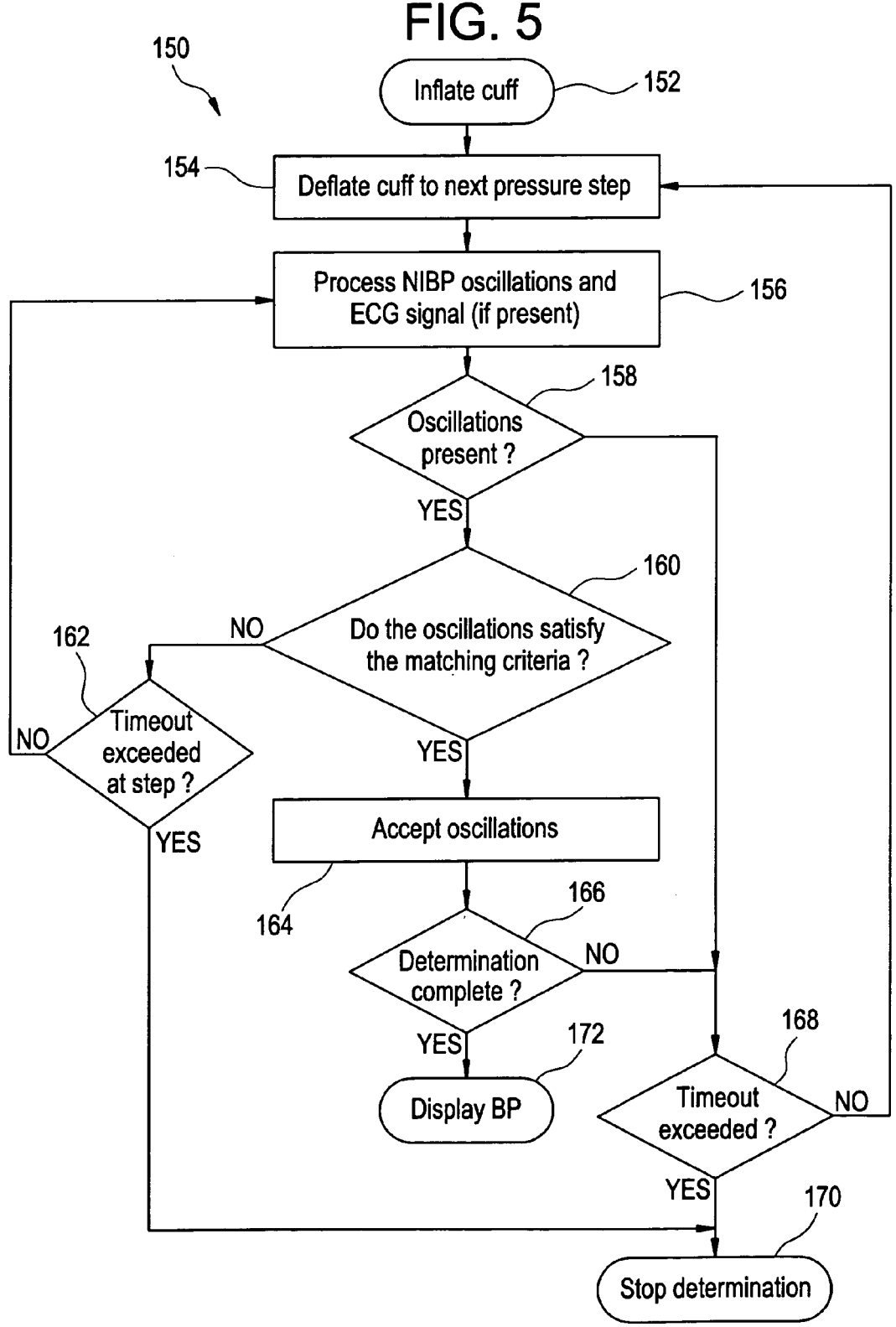

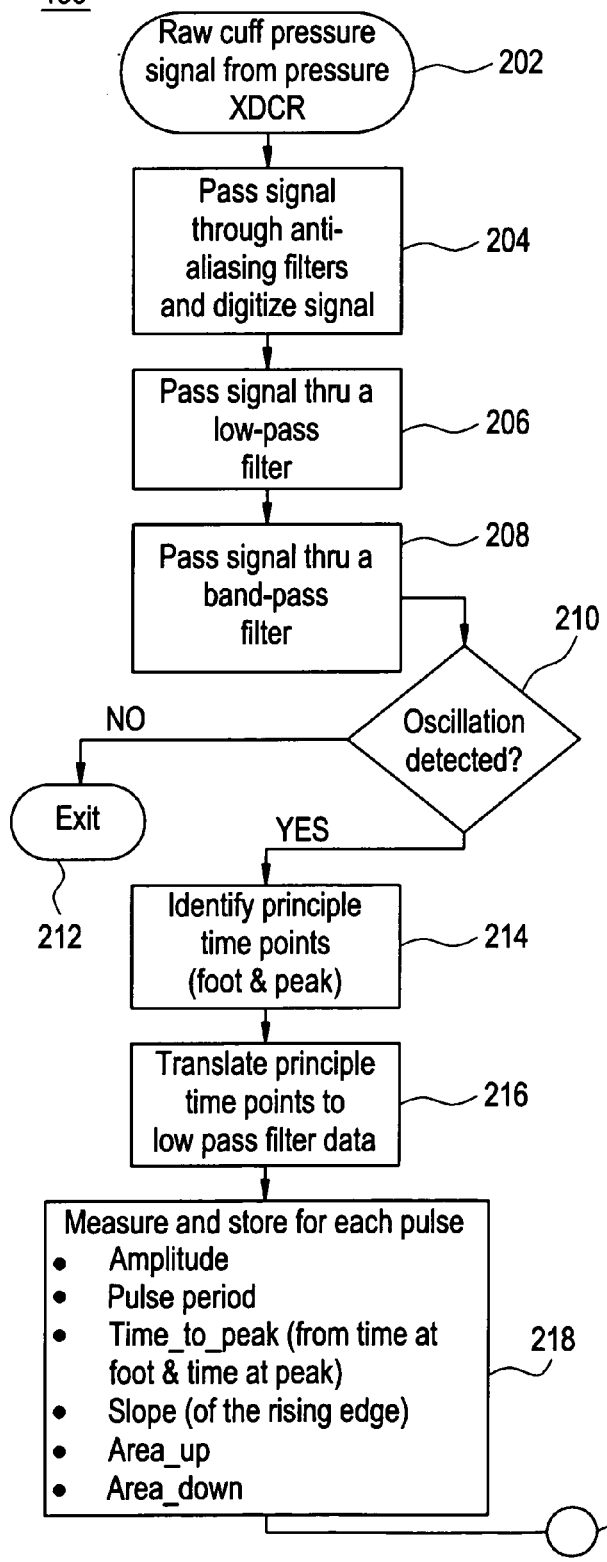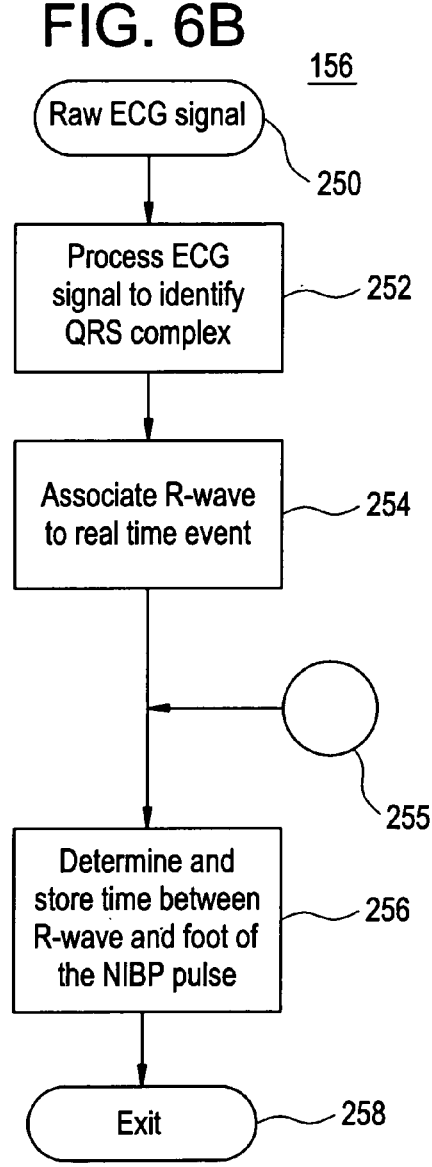
FIG. 6A
FIG. 6B

ARTIFACT REJECTION USING PULSE QUALITY VALUES

BACKGROUND OF THE INVENTION

The field of the invention is patient monitoring systems. More particularly, the invention relates to a blood pressure monitoring method and system for determining pulse rate and blood pressure of a patient.

The heart muscles of humans periodically contract to force blood through the arteries. As a result of this pumping action, pressure pulses exist in these arteries and cause them to cyclically change volume. The baseline pressure for these pulses is known as the diastolic pressure and the peak pressure for these pulses is known as the systolic pressure. A further pressure value, known as the "mean arterial pressure" (MAP), represents a time-weighted average of the blood pressure. The systolic, MAP and diastolic values for a patient are useful in monitoring the cardiovascular state of the patient, in diagnosis of a wide variety of pathological conditions, and in treating disease. Therefore, it is a great advantage to a clinician to have an automatic device which can accurately, quickly, and non-invasively estimate these blood pressure values.

There are different techniques and devices for measuring one or more of these blood pressure values. One method in particular involves applying an inflatable pressure cuff about the upper arm of a human and inflating it above systolic pressure so as to restrict the flow of blood in the brachial artery. The pressure is then slowly relieved while a stethoscope is used on the distal portion of the artery to listen for pulsating sounds, known as Korotkoff sounds, which accompany the reestablishment of blood flow in the artery. As the pressure in the cuff is reduced further, the Korotkoff sounds change and eventually disappear. The cuff pressure at which the Korotkoff sounds first appear during deflation of the cuff is an indirect measure of the systolic pressure and the pressure at which these sounds disappear is an indirect measure of the diastolic pressure. This method of blood pressure detection is generally known as the auscultatory method.

Another method of measuring blood pressure is referred to as the oscillometric technique. This method of measuring blood pressure involves applying an inflatable cuff around an extremity of a patient's body, such as the patient's upper arm. The cuff is then inflated to a pressure above the patient's systolic pressure and then reduced over time while a pressure sensor measures the cuff pressure. The sensitivity of the sensor is such that pressure fluctuations within the cuff resulting from the beats of the patient's heart may be detected. With each beat there is a resulting small change in the artery volume, which is transferred to the inflated cuff causing slight pressure variations within the cuff that are detected by the pressure sensor. The pressure sensor produces an electrical signal showing the cuff pressure and a series of small periodic variations associated with the beats of a patient's heart. It has been found that these variations, called "complexes" or "oscillations," have a peak-to-peak amplitude which is minimal for applied cuff pressures above the systolic pressure and below the diastolic pressure. As the cuff pressure is decreased from a level above the systolic pressure the oscillation size begins to monotonically grow and eventually reaches a maximum amplitude. As the cuff pressure continues to decrease past the oscillation maximum the oscillation size decreases monotonically. Physiologically, the cuff pressure at the maximum value approximates the MAP. In addition, the complex amplitudes of cuff pressures equivalent to the systolic and diastolic pressures have a relationship to this maximum value that is dependent on arterial compliance. In the majority of the population, this relationship can be approximated by a fixed ratio. Thus, the oscillometric method is based on measurements of detected complex amplitudes at various cuff pressures.

Blood pressure measuring devices operating according to the oscillometric method detect the peak-to-peak amplitude of the pressure complexes at various applied cuff pressure levels. The amplitudes of these complexes, as well as the applied cuff pressure, are stored together as the device automatically changes the cuff pressures over a range of interest. These peak-to-peak complex amplitudes define an oscillometric "envelope" and are evaluated to find the maximum value and its related cuff pressure, which is approximately equal to MAP. A cuff pressure below the MAP value that produces a peak-to-peak complex amplitude having a certain fixed relationship to the maximum value, is designated as the diastolic pressure. Likewise, a cuff pressure above the MAP value that results in complexes having an amplitude with a certain fixed relationship to that maximum value, is designated as the systolic pressure. The ratios of oscillation amplitude at the systolic and diastolic pressures to the maximum value at MAP, are empirically derived and assume varying levels depending on the preferences of those of ordinary skill in the art. Generally, these ratios are in the range of 40% to 80%.

One way to determine estimates of blood pressure is to computationally fit a curve to the oscillometric envelope defined by the complex amplitude versus cuff pressure data points which are measured by a blood pressure monitor during a determination. The fitted curve may then be used to compute an estimate of the MAP value, which is approximately at the maximum value of the fitted curve and is therefore easily determined by finding the point on the fitted curve for which the first derivative equals zero. From this maximum value data point, the systolic and diastolic pressures may be computed by finding fixed percentages of the maximum complex amplitude on the curve and using the associated cuff pressure levels as the systolic and diastolic estimates. In this manner, indirect estimates of the systolic, MAP, and diastolic arterial pressures may be found and ultimately output by an oscillometric device. The curve fitting technique has the value of smoothing the envelope information so that artifact variations are minimized and no single point dominates in the calculation of blood pressure. This results in more accurate estimates. The curve fit may also be stored for future use in estimating complex size at a given pressure level.

However, the reliability and repeatability of these computations hinges more significantly on the ability to accurately determine the magnitudes of the oscillation complexes. There are several barriers to accurate and reliable oscillation magnitude determination. First, artifacts caused by patient motion and other effects are often present. These artifacts are superimposed upon the desired oscillometric signal, causing it to be distorted. Second, the typical oscillometric non-invasive blood pressure monitor will use a band-pass filtered channel to detect and measure pulses. While this band-pass filter has the good effect of removing significant amounts of noise, it can distort the needed and true physiological components of the oscillometric signal. For example, the cut-off frequency of the high-pass portion of the band-pass filter must be set to help remove low frequency artifact, yet this same filter will also remove signal frequencies which resulted from the heart beat. This distorts the signal causing errors in measurement. Therefore, there exists the need for a system and method of effectively discriminating between true and erroneous pulse data using pulse quality values and dual channel signal processing.

SUMMARY OF THE INVENTION

One embodiment of the present invention provides a method of making pulse rate and blood pressure determinations including collecting oscillometric blood pressure data from pulses, determining and storing individual quality values for feature measurements of the pulses, obtaining an overall quality assessment based on the individual quality values, repeating the collecting step until the overall quality assessment satisfies a threshold, and determining blood pressure and pulse rate based on the oscillometric blood pressure data.

Another embodiment of the present invention provides a method of making pulse rate and blood pressure determinations including processing oscillometric waveform data by passing a cuff pressure signal through at least one filter. In addition, the method includes evaluating whether the oscillometric waveform data satisfies matching criteria including determining and storing individual quality values for feature measurements of the pulses, obtaining an overall quality assessment based on individual quality values, and collecting data until a predetermined overall quality limit is satisfied. Further, the method includes determining blood pressure and pulse rate based on the oscillometric blood pressure data.

Another embodiment of the present invention provides an apparatus for measuring blood pressure and pulse rate comprising an inflatable cuff, a pressurizing apparatus coupled to the cuff for selectively applying pressure by inflating or deflating the cuff, a cuff pressure sensor coupled to the cuff for sensing cuff pressure and blood pressure oscillations, and a programmed control device. The programmed control device may be configured to control the pressure cuff and pressurizing apparatus, collect oscillometric blood pressure data from pulses, determine individual quality values for feature measurements of the pulses, obtain an overall quality assessment based on the individual quality values, continue to collect data until the overall quality assessment satisfies a threshold, and determine blood pressure and pulse rate based on the oscillometric blood pressure data.

Another embodiment of the present invention provides a system for making pulse rate and blood pressure determinations comprising a means for collecting oscillometric blood pressure data from pulses and a means for determining and storing individual quality values for feature measurements of the pulses. In addition, the system includes a means for obtaining an overall quality value based on the individual quality values, a means for collecting data until the overall quality assessment satisfies a threshold, and a means for determining blood pressure and pulse rate based on the oscillometric blood pressure data.

Another embodiment of the present invention provides a computer program system comprising a computer useable medium having computer logic for enabling at least one processor in a computer system to make pulse rate and blood pressure determinations including a means for processing oscillometric blood pressure data by passing a cuff pressure signal through at least one filter. In addition, the computer program system includes a means for evaluating whether the oscillometric blood pressure data meets matching criteria including determining and storing associated individual quality values for feature measurements of the pulses, obtaining an overall quality assessment based on the individual quality values, and collecting data until a predetermined overall quality limit is met. Further, the computer program product includes a means for determining blood pressure and pulse rate based on the oscillometric blood pressure data.

BRIEF DESCRIPTION OF THE DRAWINGS

FIG. 3 is a flow chart of a general process for determining blood pressure and pulse rate according to an embodiment of the present invention.

FIG. 4A is a typical oscillometric complex showing how slope is determined according to an embodiment of the present invention.

FIG. 4B is a typical oscillometric complex showing how amplitude is determined according to an embodiment of the present invention.

FIG. 4C is a typical oscillometric complex showing how the amplitude is adjusted with respect to an adjusted baseline.

FIG. 4E is a typical oscillometric complex showing the area of the systolic portion and the diastolic portion of the complex according to an embodiment of the present invention.

FIG. 4F is a typical ECG signal and corresponding pressure complex.

FIG. 4H is a diagram showing a first and second pulse period relative to one another.

FIG. 5 is a flow chart of a general process for determining blood pressure and pulse rate according to an embodiment of the present invention.

FIG. 6 is a flow chart of a portion of the process for determining blood pressure and pulse rate according to an embodiment of the present invention.

DESCRIPTION OF THE PREFERRED EMBODIMENT

Figure 1:
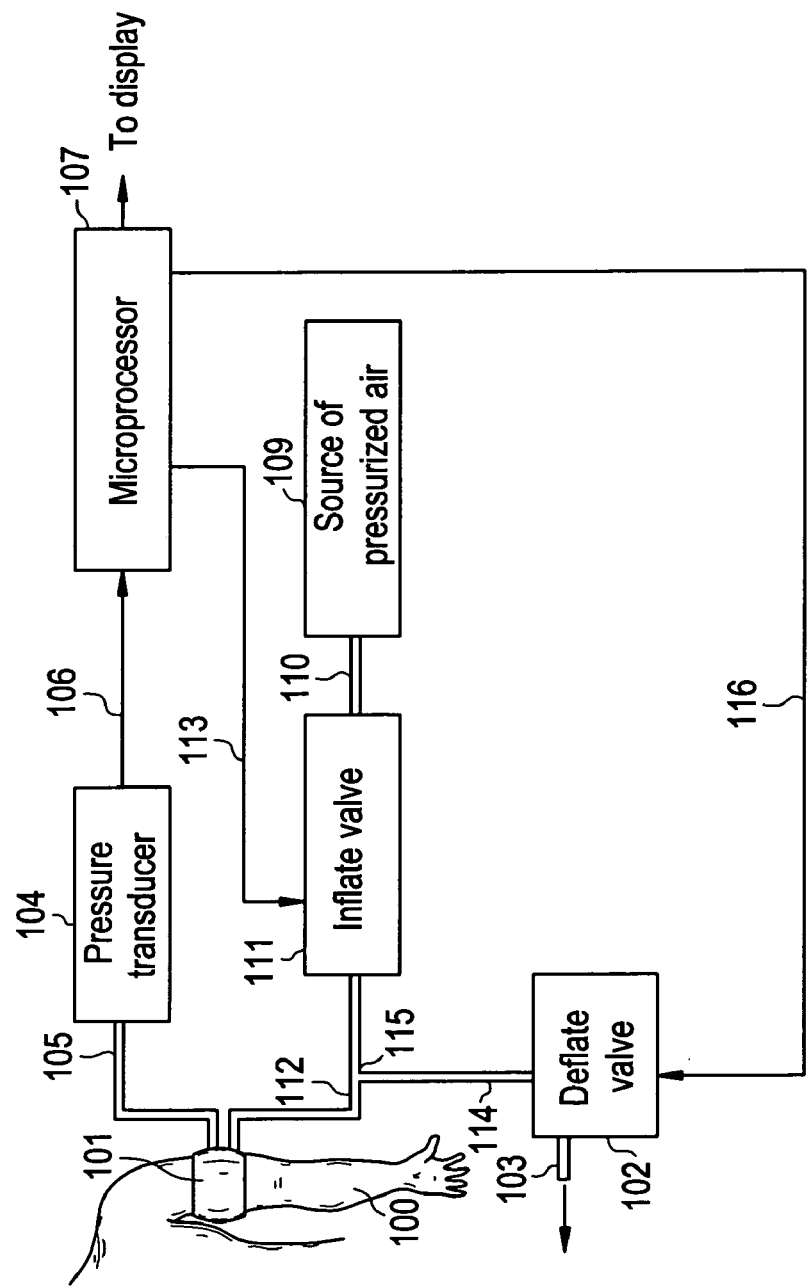
FIG. 1 is a diagram of a non-invasive blood pressure monitoring system in accordance with an embodiment of the present invention.

FIG. 1 shows the arm of a human subject wearing a conventional flexible inflatable cuff 101 capable of occluding the brachial artery when fully inflated. As cuff 101 is deflated using deflate valve 102 having exhaust 103, the arterial occlusion is gradually relieved. The deflation of cuff 101 via deflate valve 102 is controlled by microprocessor 107 via control line 116.

A pressure transducer 104 is coupled by a duct (e.g. tube, hose, etc.) 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

Figure 2:
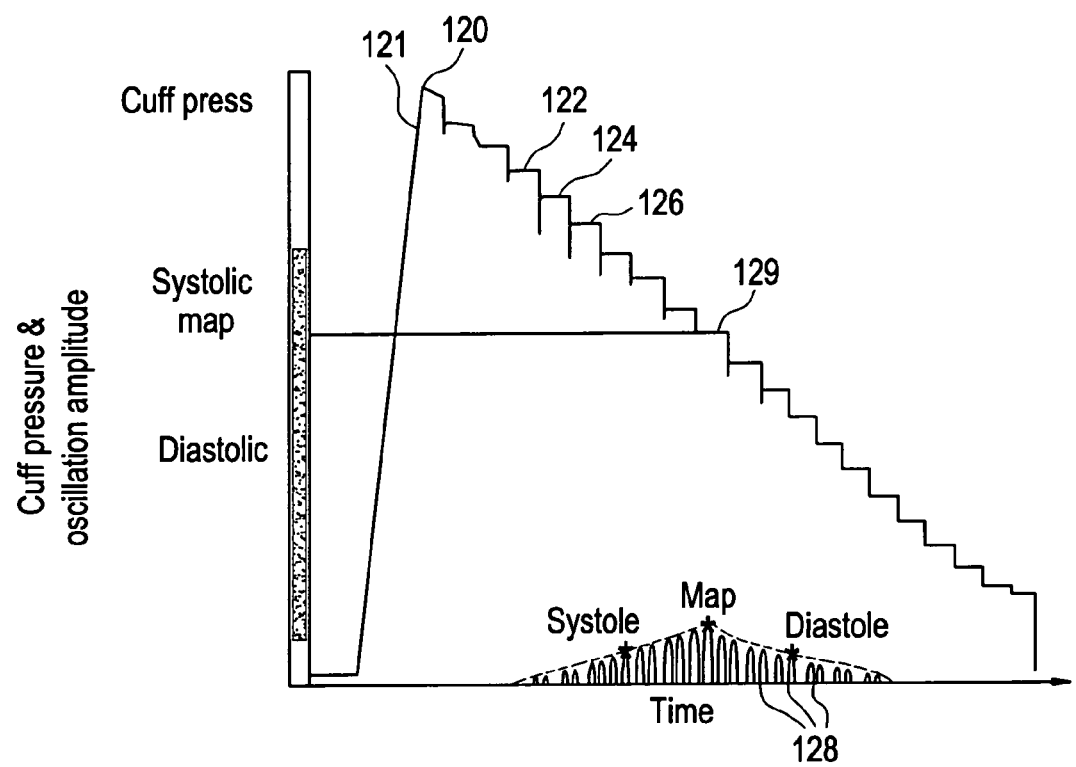
FIG. 2 displays typical waveforms for a normal oscillometric non-invasive blood pressure determination with amplitude of oscillometric pulses shown as a function of time (or cuff pressure).

FIG. 2 displays typical waveforms for a normal oscillometric non-invasive blood pressure determination with amplitude of oscillometric pulses shown as a function of time (or cuff pressure). Two waveforms are shown. Curve 121 represents the overall cuff pressure of the inflatable cuff and curve 123 represents the measured peak pulse amplitudes for oscillometric complexes. As can be seen, the cuff is first inflated to a maximum pressure 120, and then reduced in a series of small incremental steps, such as steps 122, 124, 126. Oscillations 128 corresponding to each pulse are measured at each incremental cuff pressure. The peak pulse amplitudes (PPA) of each oscillation increases with each decrement of cuff pressure until the PPA reaches a maximum at cuff pressure 129. The PPA are diminished with every subsequent reduction in cuff pressure. Thus, the cuff pressure at step 129 represents the patient's MAP, and the patient's systolic and diastolic pressures can be determined therefrom. Although FIG. 2 shows incremental decreases in pressure steps, similar determinations as those above may also be made from continuous or linear decreases in pressure over time rather than incremental steps. The technique could also be applied in a monitor that measured blood pressure on inflation.

FIG. 3 shows a general process for determining blood pressure and pulse rate according to an embodiment of the present invention. Oscillometric envelope blood pressure data is collected from pulses at step 102. The data is then filtered for detection of complexes at step 104. Associated feature measurements are then made on the minimally filtered complexes. Individual quality values (or "quality factors") are then calculated for feature measurements of the pulses at step 106. The process then obtains an overall quality assessment at step 108. In addition, the process repeats to step 102 if deemed necessary at step 110. Finally, a blood pressure and pulse rate may be determined at step 112.

The following discussion will address quality values in greater detail. Evaluation of a pulse for artifact occurs at two levels. The first is when oscillations are collected and the second is when oscillations are evaluated to produce blood pressure and pulse rate values. Each measured feature of the pulse has an associated quality value (Q), which is calculated using information from pulse oscillations of the current determination as well as information from a previous blood pressure determination. For example, measured features include average slope and amplitude. The quality value for each of these is determined using an algorithm that compares the current oscillation to previous oscillation. High quality results when the feature of a complex being evaluated has a similar magnitude as that from a different pulse or source. Low quality results when the features being compared are of a different magnitude. A quality calculation has the goal of quantifying this agreement of features. A quality calculation produces a high value when there is agreement and a low value when there is disagreement. In this way, a quality calculation has the intent of normalizing the comparisons for simpler use when making decisions about the course to take in accepting oscillometric pulses.

As the determination progresses, the quality values are updated and stored with the feature measurements. An overall quality value is calculated using a function that weights the individual quality values. The algorithm will continue to collect oscillations until the overall quality value is high enough or the maximum time at one pressure step is exceeded. Sample data, their associated feature measurements and quality factors are stored for all pulses, even ones that are rejected. When the algorithm has collected enough oscillations to attempt to produce values, the pulse data, including the quality values, are evaluated to determine blood pressure and pulse rate. At this level, one input to the decision to accept or reject oscillations are the quality values.

Some examples of quality functions are:

1. The Pulse Period Quality function (PPQ) is defined as:

$$PPQ(PP_1, PP_2) = 100 - (|PP_2 - PP_1| \times 100/PP_1)$$

where $PP_1$ is a first pulse period (e.g., pulse period 60 in FIG. 4H), and $PP_2$ is a second subsequent pulse period (e.g., pulse period 62 in FIG. 4H). The quality factor can generally take on a range of values between 0 and 100. The pulse period quality factor threshold generally used for determining if two complexes agree with each other as far as the pulse period is 70. Note that this formula provides a number that can be easily used for the decision process. A PPQ threshold of 70 requires that $PP_2$ is within +/−30% of $PP_1$ for pulse period acceptance.

2. The Peak Match Quality function (MPKQ) used to qualify pulse amplitudes at a cuff pressure is defined as:

$$MPKQ(PK_1, PK_2) = 100 - (|PK_2 - PK_1| - 3) \times 200/(PK_1 + PK_2)$$

where $PK_1$ is the amplitude of the first pulse (see FIGS. 4B and 4C), and $PK_2$ is the amplitude of the second pulse Generally, the threshold used for peak match quality is 75. This requires $0.78 \times PK_1 - 3.43 < PK_2 < 1.28 \times PK_1 + 3.43$ to be true for pulse amplitude acceptance.

3. The Slope Quality function (SLPQ) is defined as:

$$SLPQ(SLP_1, SLP_2) = 100 - (|SLP_2 - SLP_1|) \times 200/(SLP_1 + SLP_2)$$

where $SLP_1$ is a slope for a first complex (see FIG. 4A), and $SLP_2$ is a slope of a second complex. Generally, the threshold used for slope quality is 50. This means $0.60 \times SLP_1 < SLP_2 < 1.67 \times SLP_1$ must be true for slope acceptance.

4. The Time to Peak Quality function (T2PQ) is defined as $$T2PQ(T_1, T_2) = 100 - (|T_2 - T_1|) \times 200/(T_1 + T_2)$$

where $T_1$ is a time to peak for a first complex (see FIG. 4D), and $T_2$ is a time to peak for a second complex. Generally, the threshold used for slope quality is 50. This means $0.60 \times T_1 < T_2 < 1.67 \times T_1$ must be true for slope acceptance. Note that these last two quality functions are of the same form. Therefore, for many of the features that must be compared, a standard quality function can be defined as:

$$\text{Quality}(X_1, X_2) = 100 - (|X_2 - X_1|) \times 200/(X_1 + X_2)$$

5. The Last Slope Quality function (LSLPQ) is defined as:

$$LSLPQ(SLP_1, LSLP_2) = \text{Quality}(SLP_1, LSLP_2)$$

where $SLP_1$ is a slope for a first complex, and $LSLP_2$ is a slope of a second complex obtained from a previous pressure step in the determination.

6. The Last Time to Peak Quality function (LT2PQ) can be defined as:

$$LT2PQ(T2P_1, LT2P_2) = \text{Quality}(T2P_1, LT2P_2)$$

where $T2P_1$ is a time to peak for a first complex, and $LT2P_2$ is a time to peak for a second complex obtained from a previous pressure step in the determination.

7. The definition of the Envelope Quality function (ENVQ) is more complicated because different comparisons of complex size need to be used for optimal algorithm performance. Essentially, the envelope quality is a comparison between a complex size and the value predicted for the complex size using the last curve fit. The actual function used in the comparison changes at different stages of the envelope building process. In the process of computing an envelope quality the following four functions are used:

$$QNORM(X_1, X_2) = 100 - (|X_2 - X_1|) \times 100/(X_1).$$

$$QADJ1(X_1, X_2) = 100 - (|X_2 - 2 \times X_1|) \times 100/(2 \times X_1).$$

$$QADJ2(X_1, X_2) = 100 - (|X_2 - 0.875 \times X_1|) \times 100/(0.875 \times X_1).$$

$$QADJ3(X_1, X_2) = 100 - (|X_2 - 1.125 \times X_1|) \times 100/(1.125 \times X_1).$$

For the ENVQ function $X_1$ is a complex size from a first complex obtained during the present determination, and $X_2$ is a complex size obtained from using a previous curve fit to predict complex size. The computation of envelope quality consists in first deciding which stage is applicable. Stage 1 of the ENVQ is used when the cuff pressure is above the systolic value, stage 2 is used when the cuff pressure is in the neighborhood of the MAP, and stage 3 is used for all other cuff pressure levels.

For stage 1 the $ENVQ(X_1, X_2)$ is:

If $X_1 \leq X_2$, THEN $ENVQ(X_1, X_2) = QNORM(X_1, X_2)$.

If $X_2 < X_1 \leq 2 \times X_2$, THEN $ENVQ(X_1, X_2) = 100$.

If $X_1 > 2 \times X_2$, THEN $ENVQ(X_1, X_2) = QADJ1(X_1, X_2)$.

For stage 2 the $ENVQ(X_1, X_2)$ is:

If $X_1 \leq 0.5 \times X_2$, THEN $ENVQ(X_1, X_2) = 1$.

If $X_1 \geq 2 \times X_2$, THEN $ENVQ(X_1, X_2) = 1$.

If $0.5 \times X_2 < X_1 \leq 0.875 \times X_2$, THEN $ENVQ(X_1, X_2) = QADJ2(X_1, X_2)$.

If $0.875 \times X_2 < X_1 < 2 \times X_2$, THEN $ENVQ(X_1, X_2) = QADJ3(X_1, X_2)$.

For stage 3 the $ENVQ(X_1, X_2)$ is:

If $X_1 \leq 0.5 \times X_2$, THEN $ENVQ(X_1, X_2) = 1$.

If $X_1 \geq 2 \times X_2$, THEN $ENVQ(X_1, X_2) = 1$.

If $0.5 \times X_2 < X_1 < 2 \times X_2$, THEN $ENVQ(X_1, X_2) = QNORM(X_1, X_2)$.

8. An overall quality, Q, based on all of the feature measurements can be a useful calculation as a final determination as to the acceptability of a particular complex. A possible overall quality function which is a dependent on some of the individual feature qualities is:

$$Q(MPJQ, SLPQ, PPQ, ENVQ) = ([MPKQ \times SLPQ]/100 \times T2PQ]/50 + [(PPQ + ENVQ)/2])/3.$$

9. The QRS to Peak function (Q2P) is defined as:

$$QRS2P(EM_1, EM_2) = 100 - (|EM_2 - EM_1|) \times 100/EM_1$$

where $EM_1$ is a time period from R-wave in the ECG QRS complex to the peak of the oscillometric pulse (e.g., T–QRS to peak in FIG. 4F), and $EM_2$ is a time period between the same points from a subsequent pulse. The threshold generally used for determining if two complexes agree with each other as far as the QRS to peak period is 70. Note again that this formula provides a number that can be easily used for the decision process. A similar function can be computed for the period from the QRS to the foot of the complex shown in FIG. 4F.

Another measure of complex quality can be calculated from the shape of the pulse. As shown if FIG. 4E, a complex can be divided into two sections $A_S$ (43) and $A_D$, (44) which represents the area on the systolic and diastolic sections of the complex. Another measure of these areas can be computed from the area of a triangle drawn between the three points $P_{FT1}$ (46), $TP_{MAX}$ (47) and $P_{MAX}$. ($A_{ST}$) (48) and from the area of a triangle drawn between the three points $P_{FT2}$ (45), $TP_{MAX}$ (47) and $P_{MAX}$. ($A_{DT}$) (48). The ratio $A_D/A_{DT}$ defines a shape parameter. The shape parameter can change as a function of cuff pressure. For example, it may be less than one when the cuff pressure is above MAP, and greater than 1 when the cuff pressure is below MAP. However, at one cuff pressure, or at the same cuff pressure from a previous determination if the blood pressure hasn't changed, it is expected that the shape parameter should match for different pulses.

It should be noted that the quality values described above are merely exemplary. As one skilled in the art would appreciate, any number of variations of these as well as other quality values may be constructed and used.

Referring to FIG. 5, a portion of a process for determining the blood pressure and pulse rate of a patient according to an embodiment of the present invention is shown. Specifically, FIG. 5 shows process 150 for artifact rejection using pulse quality values and dual channel signal processing. The first step of the process is to inflate the cuff to a desired maximum pressure at step 152. After the cuff is inflated, it is deflated at step 154 to the next pressure step. Although an immediate deflation of the cuff occurs before any data is acquired, it will be understood that data may also be acquired during inflation or before the first deflation step is performed. Once the cuff is deflated, the non-invasive blood pressure oscillations and the ECG signal are processed at step 156. FIGS. 6A and 6B show step 156 in greater detail and are described below. After step 156 is completed, the process determines at step 158 whether any oscillations are present in the data. If there are no oscillations present, the process goes to step 168 where it evaluates whether an allotted time has been exceeded. However, if there are oscillations present, the process proceeds to step 160 where it is determined whether the oscillations satisfy specific matching criteria. Step 160 is described in greater detail in FIG. 7 and is discussed below. If the oscillations do not meet the matching criteria, the process determines at step 162 whether the allotted time has been exceeded at the pressure step (e.g., a timeout). The allotted time can vary in a particular situation according to industry standards and customs. After deflating to a new cuff pressure level a specific amount of time is allowed for searching for complexes; if no complexes are found in this period, then a step timeout occurs, no envelope information is recorded for the step, and the algorithm proceeds to deflate to a new cuff pressure level. If the allotted time has been exceeded for the pressure step, process 150 is aborted at step 170. However, if the allotted time has not been exceeded, the process returns to step 156 for non-invasive blood pressure oscillation and ECG signal processing. If the oscillations meet the matching criteria at step 160, the process accepts the oscillations at step 164. After the oscillations are accepted, the process evaluates whether the determination is complete at step 166. In other words, the process decides whether there is enough data from the oscillations to make blood pressure and pulse rate determinations. If it is decided that the determination is not complete at step 166, the process evaluates whether an allotted time has been exceeded at step 168. It is also the case that at the beginning of a determination a certain amount of time is allotted to accomplish a result. If this does not happen a determination timeout occurs which ends the determination without publishing blood pressure values. This helps guarantee the safety of the device by preventing the cuff pressure from occluding the underlying artery for a length of time which causes discomfort or injury. If an allotted time has been exceeded, the process is aborted at step 170 and the cuff is completely deflated. However, if the allotted time has not been exceeded, the process returns to step 154 where the cuff is deflated to the next pressure step. If there is enough data at step 166, the blood pressure is displayed at step 172.

FIG. 6A shows sub-steps 202–218 of step 156 for processing non-invasive blood pressure oscillations and FIG. 6B shows sub-steps 250–258 of step 156 for processing an ECG signal (if present). As shown in FIG. 6A, the raw cuff pressure signal from the pressure transducer is identified at step 202. The signal is then passed through anti-aliasing filters and is digitized at step 204. At step 206, the signal is passed through a low pass filter to eliminate noise from the signal. The cut off frequency can vary according to industry standards known by those skilled in the art. At step 208, the time sampled but otherwise raw cuff pressure signal is band-pass filtered. This band-pass filtered signal is used to help find points in time which identify where to sample the low-pass signal for measurement of pulse features. Using the two streams, the system can take advantage of the band-pass stream to find important points while making measurements on a stream that is not corrupted by the high-pass component of the band-pass filter. The process then determines whether an oscillation is detected at step 210. If an oscillation is not detected, the process exits at step 212 and proceeds to step 158 on FIG. 5. If an oscillation is detected, the process identifies principal time points at step 214. For example, the baseline and peak are examples of principal time points that may be located at step 214. At step 216, the times at which the principal points occur are transferred to the low-pass filter data. For each pulse, certain feature measurements (which will be described in detail below) are then measured and stored at step 218 including amplitude, pulse period, time to peak, slope, area up (i.e., area on systolic portion of oscillation), and area down (i.e., area on diastolic portion of oscillation). After each of these values are measured and stored, the process continues to point 255 on FIG. 6B.

An example of a feature measurement from step 218 is a determination of slope as shown in FIG. 4A. To find the slope, the low-pass signal at step 206 is first stored in a delay buffer. Next, at step 208, the band pass signal is used to identify the initial foot point. Specifically, the point immediately preceding a slope that is consistently rising for 25 msec. is identified and marked as a preliminary foot point ($P_{FOOT}$). Of course, the use of 25 msec. as a limit is merely exemplary. As one in the art would appreciate, any number of other values could be used (e.g., 20 msec., 30 msec., etc.). Next, a peak point is identified where the slope is less than 25% of the maximum slope and where the signal slope has become negative. 50% of the maximum slope is used to find the slope low point on the delay buffer signal (low pass filtered signal) (point 15 in FIG. 4A), and 25% of the maximum slope is used to find the slope high point (point 14 in FIG. 4A). The average slope is defined as the change in the oscillation waveform in going from point 15 to point 14 divided by the time between these points. This average slope is used in the computation of the slope quality function (SLPQ) described earlier. A similar process may be used to determine other feature measurements such as amplitude, time to peak, area of oscillation, etc., as described below with the following figures.

FIG. 4B shows an example of determining the amplitude of a complex. $P_{FOOT}$ is located near the beginning of the complex and the maximum peak is shown at $P_{MAX}$. The amplitude of the complex is $P_{MAX}-P_{FOOT}$.

FIG. 4C shows how to account for a drift in the signal of an oscillometric complex and correct for air effect in an initial period after a step deflation of the cuff pressure. To make the correction, the instantaneous filtered slope around the foot point is extrapolated to the time where the peak occurs and subtracted off the distance between the foot and peak. This can be found according to the following equation: $P_{MAX}-(P_{FOOT}+Tpk\times(\text{average } dP/dt))$. The maximum correction permissible is typically 25% of the distance between the foot point and the peak point. Obviously, other ways of correcting for the drift in the baseline of the signal after a step deflation of the cuff pressure can be used. For example, another way to correct for baseline drift is to compute a line from the foot point of one complex to the foot point of the subsequent complex and measure the pulse amplitude from this line to the peak of the complex.

Figure 4D:
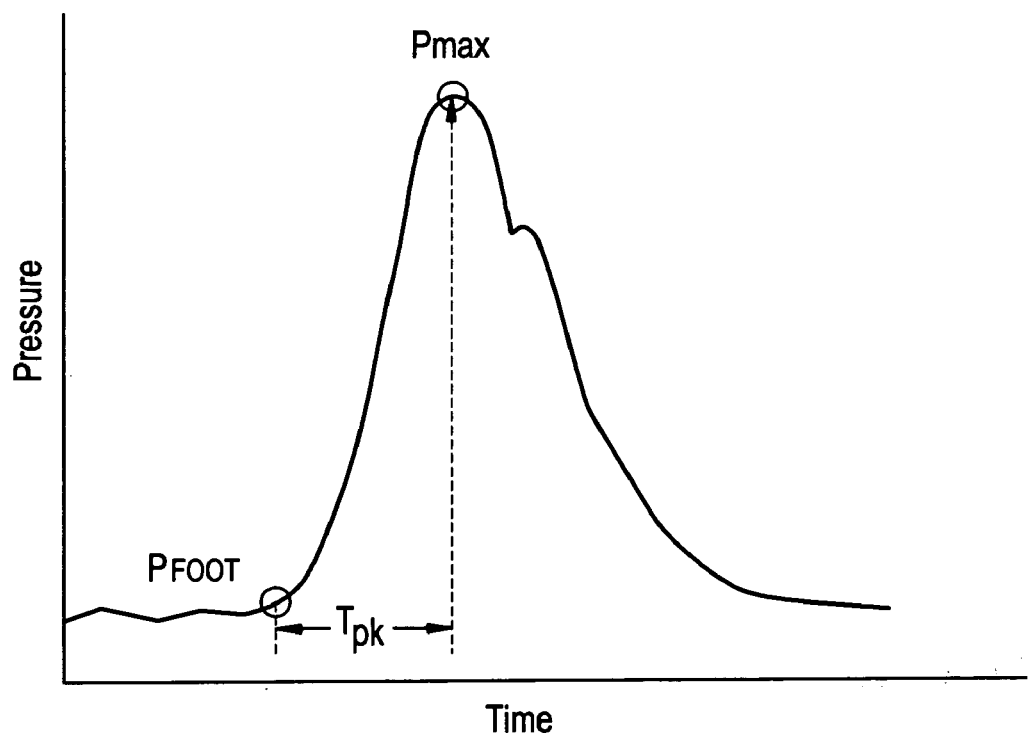
FIG. 4D is a typical oscillometric complex showing the time to peak according to an embodiment of the present invention.

FIG. 4D shows the time to peak Tpk of an oscillometric complex. The time to peak Tpk is the time from $P_{FOOT}$ to $P_{MAX}$.

FIG. 4E shows the area of the oscillometric complex. The area of the systolic portion 43 of the oscillation is shown in addition to the area of the diastolic portion 44 of the oscillation. The start of the next oscillation is shown at point 45.

FIG. 4F shows an ECG signal and corresponding pressure complex. The time measures $T_{QRS-START}$ and $T_{QRS-PK}$ used to establish the quality values are shown in the figure. These timing features can be used in the same way as other features described earlier. Additional quality functions can be defined for other features in these signals. The quality factors for these features can then be structured in similar ways to those given earlier.

Figure 4G:
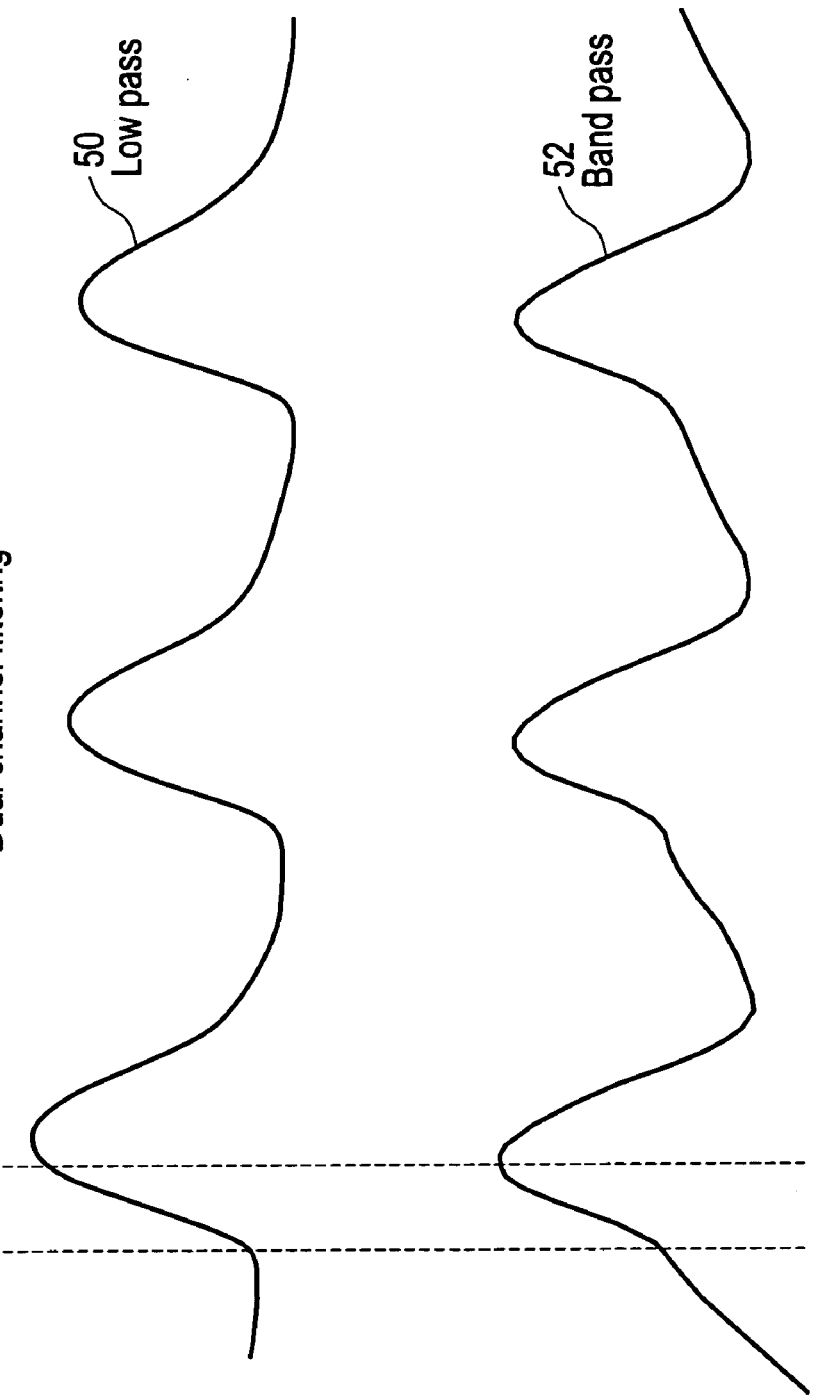
FIG. 4G is an example of dual channel filtering with low-pass and band-pass filters.

FIG. 4G shows waveforms resulting from a dual filtering technique according to an embodiment of the present invention. The blood pressure complexes 50 coming from the cuff pressure signal are low pass filtered to eliminate noise from the data. After the low pass filtering, the band pass filter is applied to signal 50 to produce the high pass signal 52. The band pass filter includes a high pass section to eliminate the baseline of the top curve 50 and allow additional points to be identified and used in various calculations.

FIG. 4H shows a first pulse period 60 and a subsequent (second) pulse period 62. Pulse period 60 can be measured between points 64 and 66 while pulse period 62 can be measured between points 68 and 70.

Referring to step 156 in FIG. 6B, ECG data (if it is acquired) is obtained at step 250. The ECG signal data is then processed to identify the QRS complex at step 252. At step 254, the R-wave is associated to the real-time event. As discussed earlier, the information from FIG. 6A is transferred to step 256 on FIG. 6B after step 254. At step 256, the time between the R-wave and the foot of the non-invasive blood pressure pulse is determined (and also time between the R-wave and the peak of the non-invasive blood pressure pulse) and stored at step 256. After this information is determined, the process exits at step 258 and proceeds to step 158 on FIG. 5.

Figure 7:
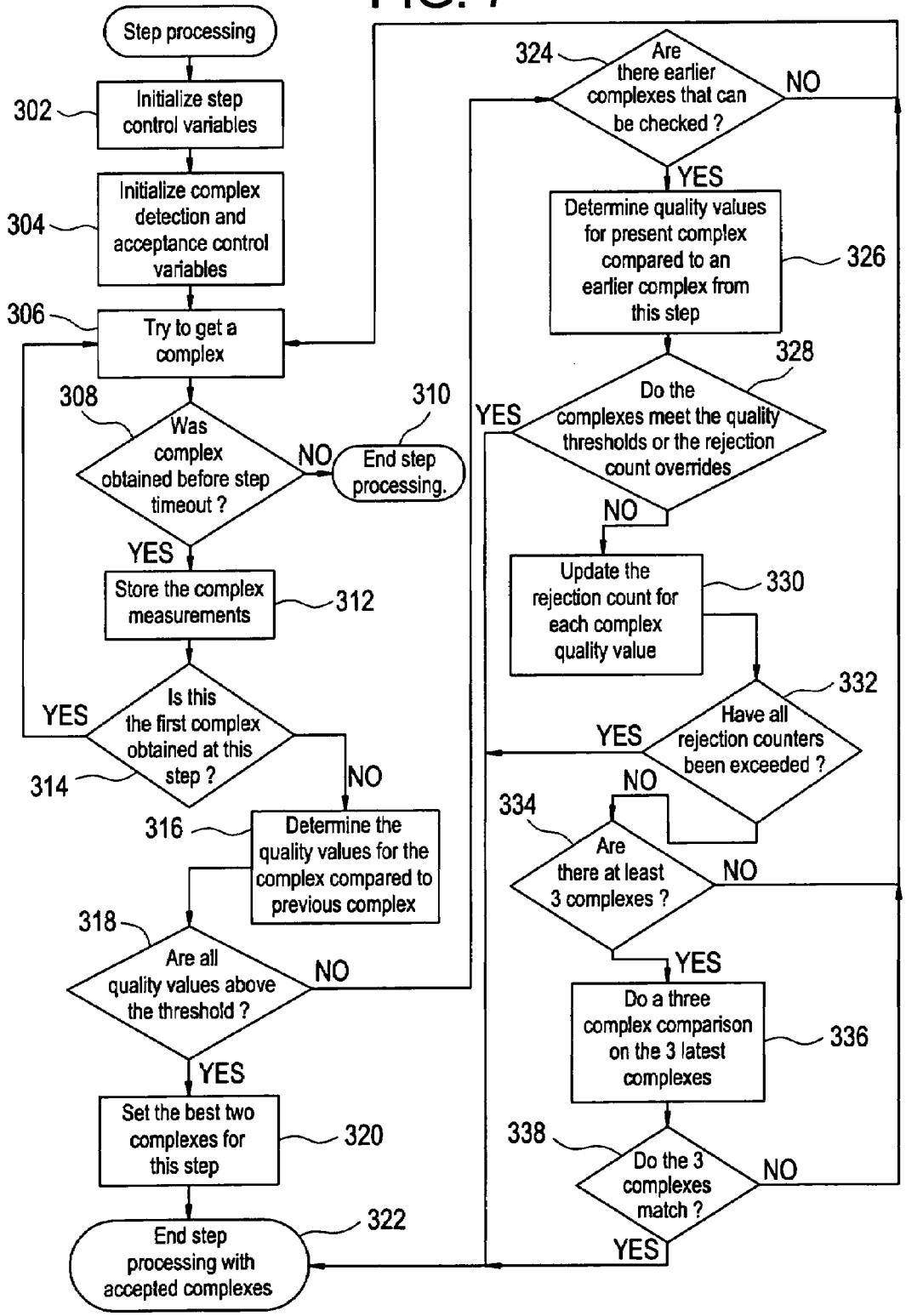
FIG. 7 is a flow chart of a portion of the process for determining blood pressure and pulse rate according to an embodiment of the present invention.

Referring to FIG. 7, process 160 shown in FIG. 5 will now be described in greater detail. Process 160 demonstrates how complexes are identified and how matching criteria is utilized. Step processing begins by initializing procedures at steps 302, 304. The step control variables are initialized at step 302 and the complex detection and acceptance control variables are initialized at step 304. The process then attempts to obtain a complex at step 306 and determine whether a complex has been obtained before a timeout at step 308. If a timeout occurs prior to obtaining a complex, the process stops step processing at step 310. If a complex is obtained, the feature measurements are stored at step 312. The feature measurements include amplitude, slope, area up, area down, time to peak and time since the QRS. After the measurements are stored, the process determines at step 314 whether the complex is the first one obtained at this step. If it is the first complex, the process returns to step 306 to obtain more complexes. If it is not the first complex (i.e., there are multiple complexes identified), the quality values for each complex are calculated at step 316. As described, quality values depend on comparisons between two complexes for each of the measurements obtained and stored.

When ECG signals are present, quality values relating to QRS timing will also be measured at step 316. Once quality values are determined, the process evaluates at step 318 whether all quality values are above predetermined thresholds. The thresholds can change depending on the circumstances of each determination. For example, one particular threshold could be used if ECG signals are present, but a different threshold could be used if ECG signals are not present (i.e., the criteria is relaxed when ECG signals are present since the use of the ECG adds requirements). If the quality values are not above the thresholds, the process determines whether there are earlier complexes that can be checked at step 324. This means that the process checks complexes other than the last (most recent) two complexes examined. If there are not any earlier complexes, the process returns to step 306. If there are earlier complexes that can be checked, the process calculates quality values at step 326 for the present complex compared to an earlier complex from the current pressure step. At step 328, the process determines whether the complexes meet the quality thresholds or the rejection count override.

The rejection count override is a mechanism that allows the determination to progress after being unable to find complexes of high quality. If a complex without an acceptable level of quality has been processed, the rejection count will be incremented. A rejection count is kept for each feature being evaluated. A rejection count will eventually exceed a threshold if pulses are repeatedly rejected, and exceeding this threshold will effectively stop the particular quality factor from rejecting the pulse. This will allow the determination to go to a new pressure step or terminate the determination, despite the inability to find high quality pulses. When this happens the algorithm will try to use the complexes with the highest overall quality to represent the oscillometric data for the step and to help in calculating blood pressure. This is a special but important use of the overall quality value. Note that the individual feature rejection counters are kept for each of the features used in evaluating complexes to provide this same relaxation function. Therefore, if either of the complexes meet the quality thresholds or the rejection count override triggers, the step processing ends at step 322. However, if the complexes do not meet the quality thresholds or rejection count override, the rejection count for each complex quality will be updated at step 330. This means the rejection count override is a way of relaxing the requirements on individual quality thresholds as time progresses at each step. Note that individual rejection counters can be kept for each of the features used in evaluating complexes providing for this same relaxation function for each feature. At step 332, the process determines whether all of the rejection counters have been exceeded. If so, the process ends step processing with accepted complexes at step 322. If all rejection counters have not been exceeded, the process determines whether there are at least three complexes at step 334. If not, the process returns to step 306 in order to get a complex. If there are at least three complexes, the process does a three complex comparison with match criteria that is high but somewhat reduced from the two complex matching requirements on the three latest complexes at step 336. The process then determines if the three complexes match at step 338. If the complexes do not match, the process returns to step 306 to get another complex. If the complexes do match, the process ends step processing with the accepted complexes at step 322.

Some examples of how quality values may be used according to different embodiments of the present invention will now be discussed. As described above with respect to operation 160, a determination is made as to whether all quality values are above the respective thresholds at step 318. For example, if PPQ>80 and SLPQ>60 and ENVQ>60 and T2PQ>60 and LSLPQ>25 and LT2PQ>25, the match criteria has been met. This match applies to a current complex and the immediately consecutive prior complex. These conditions provide the most stringent conditions on the matching process. When it happens the two best pulses for the step have been immediately identified and no further searching for complexes at the step is needed.

The next level for potential matching is for the current and any one of the previous complexes at a step. This is shown in step 324 on FIG. 7. Specifically, the process determines if MPKQ>75 and SLPQ>50 and T2PQ>50. If so, a match is identified provided ENVQ>50 and PPQ>70 and LSLPQ>25 and LT2PQ>25. Effectively, the matching criteria are slightly reduced as complexes earlier in the step are compared to the most recent. However, if a given quality value (ENVQ, PPQ, LSLPQ or LT2PQ) is failing in more than six pulses, that particular quality value is ignored provided the MPKQ is strong (i.e., >75). This allows the two best pulses to be identified even though they may not be consecutive, but this happens only after the more severe requirements as described in the previous paragraph have not been met.

Finally, there is one other criteria which will immediately indicate a matched condition for a step. This part of the algorithm is the three-pulse-match and is shown in steps 334, 336, 338 on FIG. 7. This process takes the last three pulses (P1, P2 and P3 with P3 being the most recent) and decides to match provided all of the following are satisfied: (a) the two pulse periods defined by the beginning time of the three pulses are within +/−12% of each other, (b) the amplitudes of the first and second pulse are both within +/−12% of the third pulse amplitude, (c) the slopes of the first and second pulses are within +/−12%; of the third pulse slope, (d) and the time-to-peak of the first two pulses are within 12% of the time-to-peak of the third pulse. When this match condition occurs the last two pulses obtained are taken as the two best for the step.

Even though these high quality criteria may not be satisfied, it is still possible to pick the two best pulses for a step. The best peak match part of the algorithm does this. The two best identified pulses will be taken as a match if the step should end without any of the other more difficult tests being passed. The two best pulses will be chosen if any two consecutive pulses satisfy the criteria MPKQ>75 and SLPQ>50 and T2PQ>50. However, these pulses do not have to satisfy the ENVQ>50 and PPQ>70 and LSLPQ>25 criteria. The two best pulses are then picked based on the two that have survived this loosened criteria but have the maximum overall Q for the step.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A method of making pulse rate and blood pressure determinations comprising:
    collecting oscillometric blood pressure data from pulses;
    determining individual quality values for feature measurements of the pulses;
    obtaining an overall quality assessment based on the individual quality values;
    repeating the collecting step until the overall quality assessment satisfies a threshold; and
    determining blood pressure and pulse rate based on the oscillometric blood pressure data.

2. The method of claim 1, wherein determining the individual quality values for feature measurements of the pulses comprises using information from pulse oscillations of the current determination as well as previous blood pressure determinations.

3. The method of claim 2, further comprising updating and storing the individual quality values for feature measurements, including at least one of the following measurements: (a) amplitude, (b) pulse period, (c) time to peak, (d) slope, (e) systolic area, and (f) diastolic area.

4. The method of claim 3, wherein determining individual quality values for feature measurements of the pulses comprises using a pulse period quality function according to an equation having substantially the form:

$$PPQ(PP_1, PP_2) = 100 - (|PP_2 - PP_1| \times 100/PP_1)$$

where $PP_1$ is a first pulse period and $PP_2$ is a second subsequent pulse period.

5. The method of claim 3, wherein determining individual quality values for feature measurements of the pulses comprises using a peak match quality function according to an equation having substantially the form:

$$MPKQ(PK_1, PK_2) = 100 - (|PK_2 - PK_1| - 3) \times 200/(PK_1 + PK_2)$$

where $PK_1$ is an amplitude of a first pulse and $PK_2$ is an amplitude of a second pulse.

6. The method of claim 3, wherein determining individual quality values for feature measurements of the pulses comprises using a slope quality function according to an equation having substantially the form:

$$SLPQ(SLP_1, SLP_2) = 100 - (|SLP_2 - SLP_1|) \times 200/(SLP_1 + SLP_2)$$

where $SLP_1$ is a slope for a first complex and $SLP_2$ is a slope of a second complex.

7. The method of claim 3, wherein determining individual quality values for feature measurements of the pulses comprises using a time to peak quality function according to an equation having substantially the form:

$$T2PQ(T_1, T_2) = 100 - (|T_2 - T_1|) \times 200/(T_1 + T_2)$$

where $T_1$ is a time to peak for a first complex and $T_2$ is a time to peak for a second complex.

8. The method of claim 3, wherein determining individual quality values for feature measurements of the pulses comprises using a last slope quality function according to an equation having substantially the form:

$$LSLPQ(SLP_1, LSLP_2) = \text{Quality}(SLP_1, LSLP_2)$$

where $SLP_1$ is a slope for a first complex and $LSLP_2$ is a slope of a second complex obtained from a previous pressure step in the determination.

9. The method of claim 3, wherein determining individual quality values for feature measurements of the pulses comprises using a last time to peak quality function according to an equation having substantially the form:

$$LT2PQ(T2P_1, LT2P_2) = \text{Quality}(T2P_1, LT2P_2)$$

where $T2P_1$ is a time to peak for a first complex and $LT2P_2$ is a time to peak for a second complex obtained from a previous pressure step in the determination.

10. The method of claim 3, wherein determining individual quality values for feature measurements of the pulses comprises using an envelope quality function according to an equation having substantially the form:

$$QNORM(X_1, X_2) = 100 - (|X_2 - X_1|) \times 100/(X_1)$$

$$QADJ1(X_1, X_2) = 100 - (|X_2 - 2 \times X_1|) \times 100/(2 \times X_1)$$

$$QADJ2(X_1, X_2) = 100 - (|X_2 - 0.875 \times X_1|) \times 100/(0.875 \times X_1)$$

$$QADJ3(X_1, X_2) = 100 - (|X_2 - 1.125 \times X_1|) \times 100/(1.125 \times X_1)$$

where $X_1$ is a complex size from a first complex obtained during a present determination and $X_2$ is a complex size obtained from using a previous curve fit to predict complex size.

11. The method of claim 10, wherein the envelope quality function is determined according to the following statements when cuff pressure is above systolic value:

If $X_1 \leq X_2$, THEN $ENVQ(X_1, X_2) = QNORM(X_1, X_2)$

If $X_2 < X_1 \leq 2 \times X_2$, THEN $ENVQ(X_1, X_2) = 100$

If $X_1 > 2 \times X_2$, THEN $ENVQ(X_1, X_2) = QADJ1(X_1, X_2)$ where $X_1$ is a complex size from a first complex obtained during a present determination and $X_2$ is a complex size obtained from using a previous curve fit to predict complex size.

12. The method of claim 10, wherein the envelope quality function is determined according to the following statements when cuff pressure approximates MAP value:

If $X_1 \leq 0.5 \times X_2$, THEN $ENVQ(X_1, X_2) = 1$

If $X_1 \geq 2 \times X_2$, THEN $ENVQ(X_1, X_2) = 1$

If $0.5 \times X_2 < X_1 \leq 0.875 \times X_2$, THEN $ENVQ(X_1, X_2) = QADJ2(X_1, X_2)$ If $0.875 \times X_2 < X_1 < 2 \times X_2$, THEN $ENVQ(X_1, X_2) = QADJ3(X_1, X_2)$ where $X_1$ is a complex size from a first complex obtained during a present determination and $X_2$ is a complex size obtained from using a previous curve fit to predict complex size.

13. The method of claim 10, wherein the envelope quality function is determined according to the following statements when cuff pressure is not above systolic and not near MAP:

If $X_1 \leq 0.5 \times X_2$, THEN $ENVQ(X_1,X_2)=1$

If $X_1 \geq 2 \times X_2$, THEN $ENVQ(X_1,X_2)=1$

If $0.5 \times X_2 < X_1 < 2 \times X_2$, THEN $ENVQ(X_1,X_2)=QNORM(X_1,X_2)$ where $X_1$ is a complex size from a first complex obtained during a present determination and $X_2$ is a complex size obtained from using a previous curve fit to predict complex size.

14. The method of claim 3, wherein obtaining the overall quality assessment based on the individual quality values comprises using an equation having substantially the form:

$Q(MPJQ,SLPQ,PPQ,ENVQ)=[(MPKQ \times SLPQ)/100 \times T2PQ]/50+[(PPQ+ENVQ)/2])/3$ where Q(MPJQ, SLPQ, PPQ, ENVQ) is an overall quality value, MPKQ is a peak match quality value, SLPQ is a slope quality value, PPQ is a pulse period quality value, and ENVQ is an envelope quality value.

15. The method of claim 1, wherein determining individual quality values for feature measurements of the pulses comprises using a QRS to Peak function according to an equation having substantially the form:

$QRS2P(EM_1,EM_2)=100-(|EM_2-EM_1|) \times 100/EM_1$ where $EM_1$ is a time period from R-wave in the ECG QRS complex to the peak of the oscillometric pulse (e.g., T-QRS to peak in FIG. 4F), and $EM_2$ is a time period between the same points from a subsequent pulse.

16. The method of claim 1, wherein determining individual quality values for feature measurements of the pulses comprises using a QRS to start function according to an equation having substantially the form:

$QRS2F(EM_1,EM_2)=100-(|EM_2-EM_1|) \times 100/EM_1$ where $EM_1$ is a time period from R-wave in the ECG QRS complex to the start of the oscillometric pulse (e.g., T–QRS to start in FIG. 4F), and $EM_2$ is a time period between the same points from a subsequent pulse.

17. The method of claim 1, further comprising rejecting pulses with individual quality values that do not meet threshold limits.

18. A method of making pulse rate and blood pressure determinations comprising:
processing oscillometric waveform data by passing a cuff pressure signal through at least one filter;
evaluating whether the oscillometric waveform data satisfies matching criteria including determining individual quality values for feature measurements of pulses, obtaining an overall quality assessment based on the individual quality values, and collecting data until a predetermined overall quality limit is satisfied; and
determining blood pressure and pulse rate based on the oscillometric waveform data.

19. The method of claim 18, wherein the evaluating step further comprises updating and storing the individual quality values during a current determination.

20. The method of claim 19, wherein determining the individual quality values for feature measurements of the pulses comprises using information from pulse oscillations of the current determination as well as previous blood pressure determinations.

21. The method of claim 18, wherein the evaluating step further comprises updating and storing the individual quality values for feature measurements including at least one of the following measurements: (a) amplitude, (b) pulse period, (c) time to peak, (d) slope, (e) systolic area, and (f) diastolic area.

22. The method of claim 18, wherein the evaluating step further comprises rejecting pulses with individual quality values that do not satisfy threshold limits.

23. The method of claim 18, wherein the processing step comprises passing a cuff pressure signal through a low-pass filter for eliminating noise from the signal, thereby creating low-pass filter data.

24. The method of claim 23, further comprising passing the signal through a band-pass filter for locating at least one principal time point in the signal.

25. The method of claim 24, further comprising transferring the time of at least one principal time point of the band-pass filter to the low-pass filter data to help identify and estimate features of that low-pass filtered signal.

26. The method of claim 18, further comprising processing an ECG signal.

27. The method of claim 26, further comprising using the ECG signal in evaluating the oscillometric blood pressure data.

28. An apparatus for measuring blood pressure and pulse rate comprising:
an inflatable cuff;
a pressurizing apparatus coupled to the cuff for selectively applying pressure by inflating or deflating the cuff;
a cuff pressure sensor coupled to the cuff for sensing cuff pressure and blood pressure oscillations;
a programmed control device configured to control the pressure cuff and pressurizing apparatus, collect oscillometric blood pressure data from pulses, determine individual quality values for feature measurements of the pulses, obtain an overall quality assessment based on the individual quality values, continue to collect data until the overall quality assessment satisfies a threshold, and determine blood pressure and pulse rate based on the oscillometric blood pressure data.

29. The apparatus of claim 28, wherein the programmed control device is configured to determine the individual quality values for feature measurements of the pulses based on information from pulse samples of the current determination as well as previous blood pressure determinations.

30. The apparatus of claim 29, wherein the programmed control device is configured to determine the individual quality values for feature measurements including at least one of the following measurements: (a) amplitude, (b) pulse period, (c) time to peak, (d) slope, (e) systolic area, and (t) diastolic area.

31. The apparatus of claim 30, wherein the programmed control device is configured to reject pulses with individual quality values that do not satisfy threshold limits.

32. The apparatus of claim 28, wherein the programmed control device is further configured to process an ECG signal to evaluate the oscillometric blood pressure data.

33. The apparatus of claim 28, wherein the programmed control device is further configured to pass a cuff pressure signal through a low-pass filter to eliminate noise from the signal and thereby create low-pass filter data, and pass the signal through a band-pass filter for locating at least one principal time point in the signal.

34. The apparatus of claim 33, wherein the programmed control device is further configured to translate at least one key point in time to the low-pass filter data, and to measure and store for one or more complexes at least one of the following feature measurements: (a) amplitude, (b) pulse period, (c) time to peak, (d) slope, (e) systolic area, and (f) diastolic area.

35. A system for making pulse rate and blood pressure determinations comprising:
   means for collecting oscillometric blood pressure data from pulses;
   means for determining individual quality values for feature measurements of the pulses;
   means for obtaining an overall quality assessment based on function that weights the individual quality values;
   means for collecting data until the overall quality assessment satisfies a threshold; and
   means for determining blood pressure and pulse rate based on the oscillometric blood pressure data.

36. A computer program system comprising:
   a computer useable medium having computer logic for enabling at least one processor in a computer system to make pulse rate and blood pressure determinations;
   means for processing oscillometric blood pressure data by passing a cuff pressure signal through at least one filter;
   means for evaluating whether the oscillometric blood pressure data meets matching criteria including determining associated individual quality values for feature measurements of the pulses, obtaining an overall quality assessment based on the individual quality values, and collecting data until a predetermined overall quality limit is met; and
   means for determining blood pressure and pulse rate based on the oscillometric blood pressure data.

* * * * *